United States Patent
Musani

(10) Patent No.: US 8,512,414 B2
(45) Date of Patent: Aug. 20, 2013

(54) AIRWAY ANCHOR SUTURE TO PREVENT AIRWAY STENT MIGRATION

(75) Inventor: Ali I. Musani, Centennial, CO (US)

(73) Assignee: National Jewish Health, Denver, CO (US)

( * ) Notice: Subject to any disclaimer, the term of this patent is extended or adjusted under 35 U.S.C. 154(b) by 169 days.

(21) Appl. No.: 13/043,870

(22) Filed: Mar. 9, 2011

(65) Prior Publication Data

US 2011/0230974 A1    Sep. 22, 2011

Related U.S. Application Data

(60) Provisional application No. 61/314,928, filed on Mar. 17, 2010.

(51) Int. Cl.
*A61F 2/06* (2013.01)

(52) U.S. Cl.
USPC ........................................... 623/23.7

(58) Field of Classification Search
USPC ...................... 623/1.11–1.42, 23.7
See application file for complete search history.

(56) References Cited

U.S. PATENT DOCUMENTS

| | | | |
|---|---|---|---|
| 4,794,924 A | | 1/1989 | Eliachar |
| 5,017,188 A | * | 5/1991 | Marten et al. ................. 604/178 |
| 5,297,546 A | * | 3/1994 | Spofford et al. ......... 128/207.14 |
| 7,025,784 B1 | | 4/2006 | Blom et al. |
| 7,195,016 B2 | * | 3/2007 | Loyd et al. ............... 128/207.14 |
| 7,547,321 B2 | * | 6/2009 | Silvestri et al. .............. 623/1.15 |
| 2003/0028255 A1 | * | 2/2003 | Hartig et al. .................. 623/23.7 |
| 2004/0148032 A1 | * | 7/2004 | Rutter et al. .................. 623/23.7 |
| 2005/0177233 A1 | | 8/2005 | Monnier et al. |
| 2007/0198074 A1 | * | 8/2007 | Dann et al. ................... 623/1.11 |
| 2009/0312603 A1 | * | 12/2009 | Lam et al. ..................... 600/106 |
| 2010/0286791 A1 | | 11/2010 | Goldsmith |
| 2011/0270031 A1 | * | 11/2011 | Frazier et al. .................. 600/37 |

OTHER PUBLICATIONS

International Search Report for International (PCT) Patent Application No. PCT/US2011/027688, mailed May 13, 2011 3 pages.
Written Opinion for International (PCT) Patent Application No. PCT/US2011/027688, mailed May 13, 2011 6 pages.

* cited by examiner

*Primary Examiner* — Suzette J Gherbi
(74) *Attorney, Agent, or Firm* — Sheridan Ross PC

(57) ABSTRACT

An airway stent with an integral suture anchor is used to prevent migration of the stent within the airway. The suture anchor is incorporated by percutaneous placement of a suture through the neck and into the stent. The distal end of the suture includes an anchor element to secure the suture to the stent. The opposite end of the suture is tensioned and held in place by a suture clamp and a pledget routed over the stent and placed against the neck. Airway stents such as tracheal stents are effective at maintaining airway patency however; a common complication is stent migration. The integral suture anchor provides a reliable, economical, and non-intrusive solution to stent migration.

5 Claims, 5 Drawing Sheets

AIRWAY ANCHOR SUTURE TO PREVENT AIRWAY STENT MIGRATION

CROSS REFERENCE TO RELATED APPLICATIONS

This application claims priority to U.S. Provisional Patent Application No. 61/314,928 filed on Mar. 17, 2010, which is hereby incorporated in its entirety by reference.

FIELD OF THE INVENTION

The present invention relates to medical stents and methods of anchoring stents, and more particularly, to an airway anchor suture especially adapted for anchoring an airway stent such as a tracheal stent, and a method of emplacement of the airway anchor suture.

BACKGROUND OF THE INVENTION

Tracheal and airway stenosis can be caused by a number of reasons to include tissue reaction from a tracheostomy or endotracheal intubation. Tracheal stenosis can also be caused by collagen vascular diseases and malignant conditions of the airways. In some cases, a short segment stenosis can be treated with surgical resection. Complex stenosis, long stenosis, and stenosis occurring at the very proximal portion of the trachea are not effectively treatable with surgical resection, and therefore require treatment via a rigid or flexible bronchoscope.

Bronchoscopic therapies include laser excision, balloon dilation, and rigid bronchoscopic dilation, injection of corticosteroids, topical mitomycin-C and silicone stent placement. Silicone stents are effective at maintaining airway patency; however, one of the known complications is stent migration. Stent migration can be particularly problematic when a stent is placed in the proximal subglottic space.

One known solution to prevent tracheal stent migration is the incorporation of a plurality of protrusions or studs on the outer surface of the stent. Over a period of time, these studs/protrusions will seat into the tracheal wall to help prevent migration, however, a tracheal stent is very prone to migration prior to seating of the studs. Further, inflammation of the trachea may be exacerbated by migration of the stent in which the studs may cause greater frictional contact with the tracheal wall as the stent migrates.

Therefore, there is a need to provide a safe and effective means for securing tracheal airway stents in the proximal airway or tracheal space without migration. Further, there is a need to anchor the stents in a non-obtrusive manner that does not further irritate the tracheal wall.

SUMMARY OF THE INVENTION

In accordance with the present invention, apparatuses and a method are provided for stabilizing and securing an airway stent to include tracheal stents. In one aspect of the invention, an anchor apparatus includes an anchor suture that is anchored at one end to the inside wall of a stent, and the other end of the suture extends through the patient's neck. The end of the suture anchor placed inside the stent includes a rigid cross-member or T-bar member to prevent the suture from being disconnected from engagement with the stent. The exposed portion of the suture outside of the patient's neck is secured by a pad, such as a cotton pledget, silicone or rubber button/pad that is fitted over the suture. A washer and one or more clamps hold the suture against the pledget, button or pad. The term "pad" used hereinafter shall be understood to also cover pledgets, and buttons, and other equivalent structures.

In another aspect of the invention, the apparatus may be considered the combination of a stent and airway anchor. The stent used with the airway anchor can include any number of different types of existing stents to include silicone stents or stents made from other materials.

In use, the pledget along with the washer and clamp(s) are slid along the suture until the pledget contacts the neck. The suture is tightened, and the washer and clamp(s) secure the end of the suture to the pledget. Excess suture extending beyond the clamp(s) is cut. In lieu of a clamp, the end of the suture can be tied in a knot against the washer.

According to the method of the present invention, a patient to receive a tracheal stent is preferably placed under general anesthesia. An endoscope such as a rigid bronchoscope may be used to first treat the stenosis and/or balloon dilation can be conducted prior to placement of the tracheal stent. The tracheal stent can be deployed in a known manner, such as utilizing a stent deployment plunger to locate the stent to cover the affected area of the trachea. Placement can be adjusted with rigid forceps. The T-bar of the suture is loaded in the open distal end of a hollow introducer needle. The needle is inserted through the neck of the patient and through the wall of the stent. The T-bar is deployed with a stylet that is inserted through the cannula of the needle. Once the T-bar is freed from the needle, the needle is removed from the neck, and the suture is tightened so the T-bar is flush with the interior surface of the stent. The pledget is slid along the suture and is positioned against the neck. The pledget is pressed against the neck to tension the suture, and the clamp(s) are activated to secure the suture. Excess suture is clipped.

Other features and advantages of the invention will become apparent from a review of the following detailed description, taken in conjunction with the figures.

DETAILED DESCRIPTION

Figure 1:
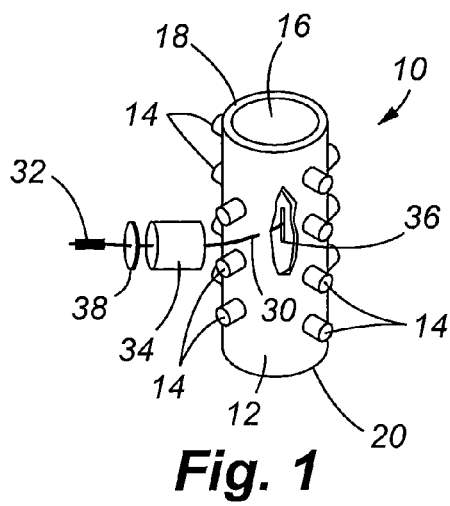
FIG. 1 is a perspective view illustrating the tracheal stent with integral suture anchor of the present invention, wherein a portion of the wall of the stent is cut away to view the T-bar secured within the inner diameter of the stent.

FIG. 1 illustrates the tracheal stent and integral suture anchor of the present invention. The tracheal stent with anchor 10 is more particularly shown as a stent having a tubular shaped body 12 with proximal 18 and distal 20 ends extending substantially transversely to a longitudinal axis or length of the stent body 12. Optionally, a plurality of studs or protrusions 14 may be disposed on the exterior surface of the stent in order to help secure the stent within the trachea of the patient in which the studs become seated or partially embedded in the tracheal wall.

A suture anchor comprises a length of suture 30 having a T-bar member 36 attached to one end that serves to anchor the suture 30 within the body 12. The T-bar member extends transversely to the length of the suture 30. As explained below with respect to the method, the T-bar 36 is placed the interior open space of the stent 10 and against the interior surface 16 of the stent body 12. The cut away portion in FIG. 1 illustrates the length of suture extending through the wall of the stent body 12 thereby placing the T-bar 36 in the open space within the stent. A flexible pad, such as a cotton pledget 34, has a central opening to receive the suture 30. A washer or bearing member 38 having a central opening receives the suture and the washer 38 is placed next to the pledget. One or more suture clamps 32 receive the suture 30 and the clamp(s) are tightened against the exposed surface of the washer 38 to compress and hold the pledget 34 when the suture is tightened. The washer 38 is optional and can be made of material more rigid than the pledget 34.

Figure 2:
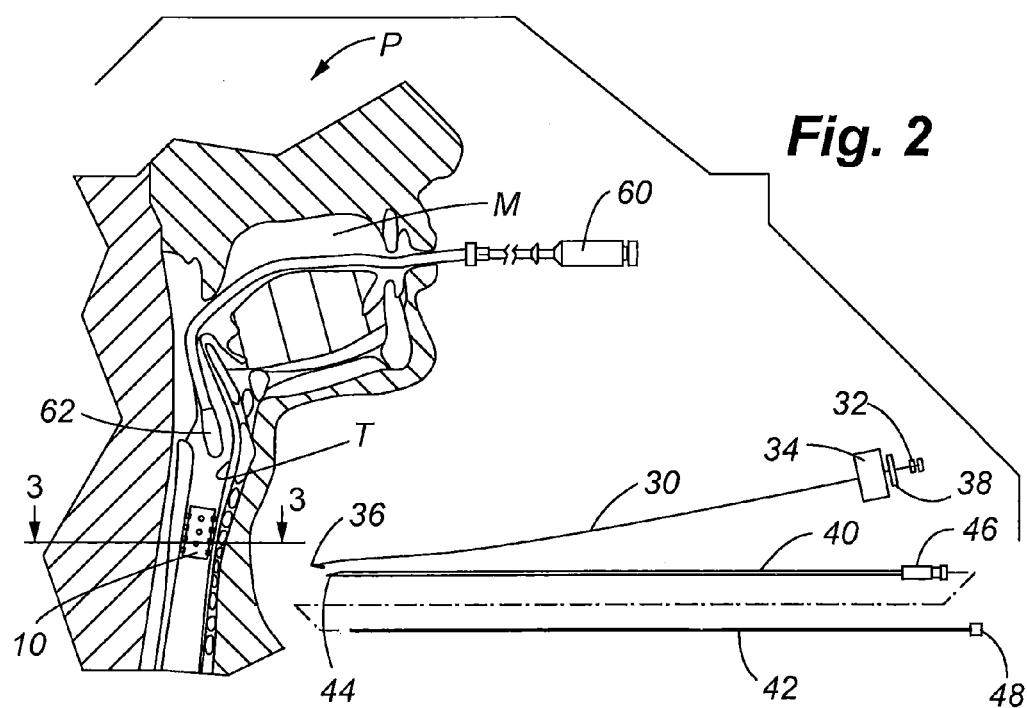
FIG. 2 is a vertical cross-section showing a patient with a tracheal stent emplaced in the trachea, such as within the proximal subglottic space, and further showing an introducer needle in preparation for connecting the suture anchor to the stent.

Referring to FIG. 2, a patient P is illustrated in which the stent has been placed in the trachea T of the patient. As mentioned, the stent can be emplaced according to known methods such as by a stent deployment plunger to locate the stent to cover the affected area of the trachea. An endoscope such as a rigid bronchoscope may be used to first treat the stenosis and/or balloon dilation can be conducted prior to placement of the tracheal stent. As shown in the figure, a bronchoscope 60 having a video camera disposed at the distal end 62 of the bronchoscope may be used for visualization of the stent and the procedure that follows to secure the suture anchor to the stent. The bronchoscope 60 is illustrated extending through the patient's mouth M, but it shall be understood that the bronchoscope 60 can also be placed through the nasal passages, depending upon the type of scope used and the preference of the practitioner.

Figure 3:
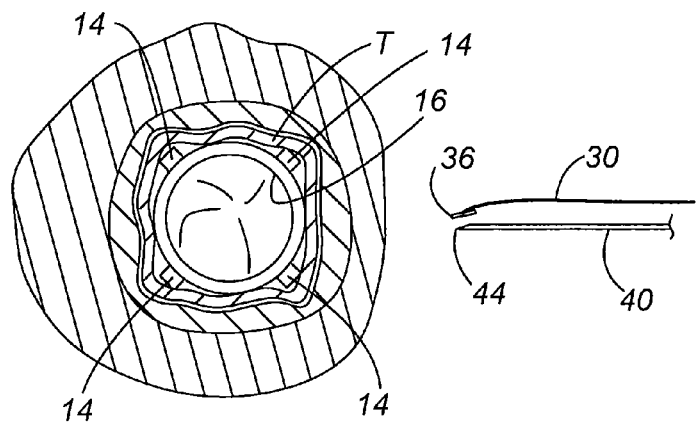
FIG. 3 is a greatly enlarged horizontal section taken along line 3-3 of FIG. 2 illustrating a portion of the patient's neck with the stent placed in the trachea and further illustrating the distal end of the introducer needle and the suture anchor in preparation for penetrating the neck.

FIGS. 2 and 3 also illustrate the suture anchor and how it may be loaded within the open distal end 44 of an introducer needle 40. The T-bar 36 of the suture 30 is oriented for insertion in the open end, and the suture is then pulled tight and held against the outer surface of the introducer needle 40. Optionally, a stylet 42 can be inserted within the open proximal end 46 of the introducer needle 40 in order to deploy the T-bar 36 as discussed below.

Figure 4:
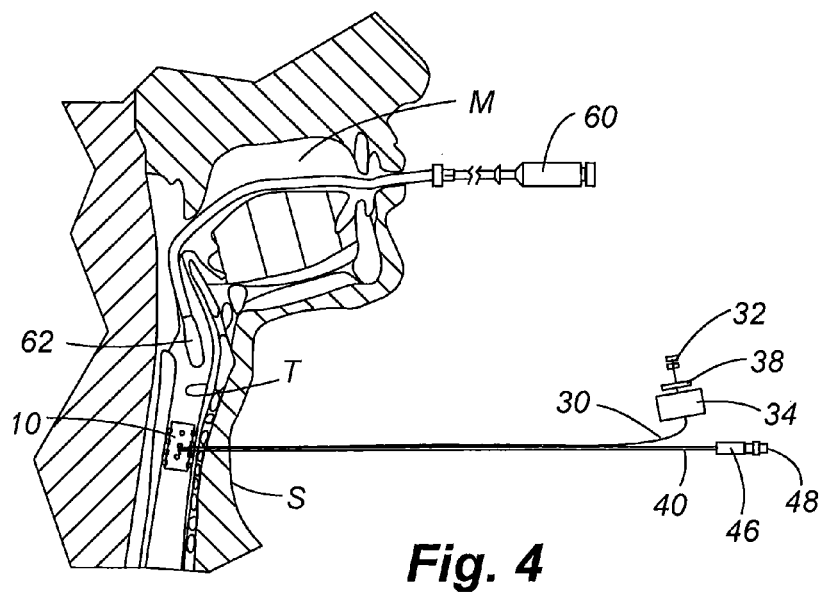
FIG. 4 is another vertical section illustrating the T-bar of the suture anchor secured to the introducer needle, and the introducer needle placed through the patient's neck into the stent.
Figure 5:
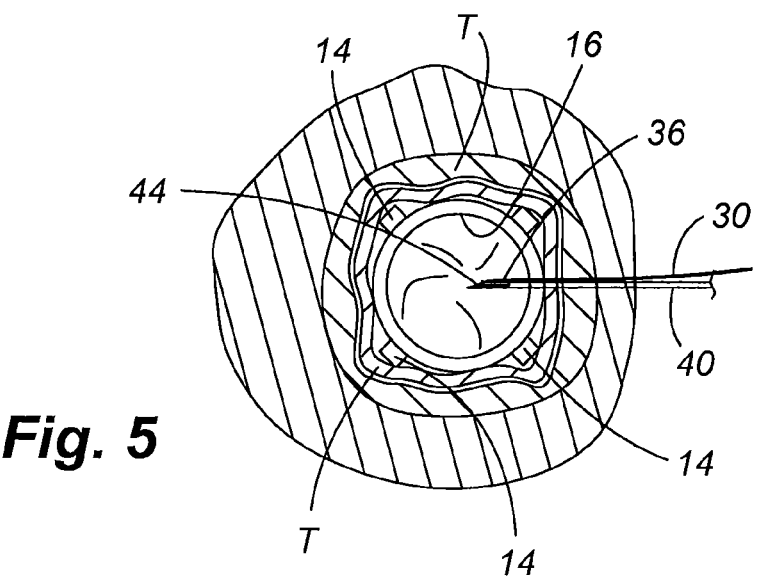
FIG. 5 is another horizontal section showing the needle extending through the neck and through the wall of the stent with the distal end of the needle within the hollow open interior of the stent.

Referring now to FIGS. 4 and 5, once the T-bar 36 is loaded within the distal end 44 of the needle 40, the introducer needle is placed through the neck of the patient and the distal end of the needle 44 is placed within the hollow space or gap within the stent as shown in FIG. 5. Under bronchoscopic visualization, a practitioner can easily view the location of the distal end of the introducer needle.

To deploy the T-bar 36 and to thereby separate the T-bar 36 from the introducer needle, the stylet 42 is inserted within the introducer needle thereby pushing the T-bar 36 out of the cannula of the introducer needle.

Figure 6:
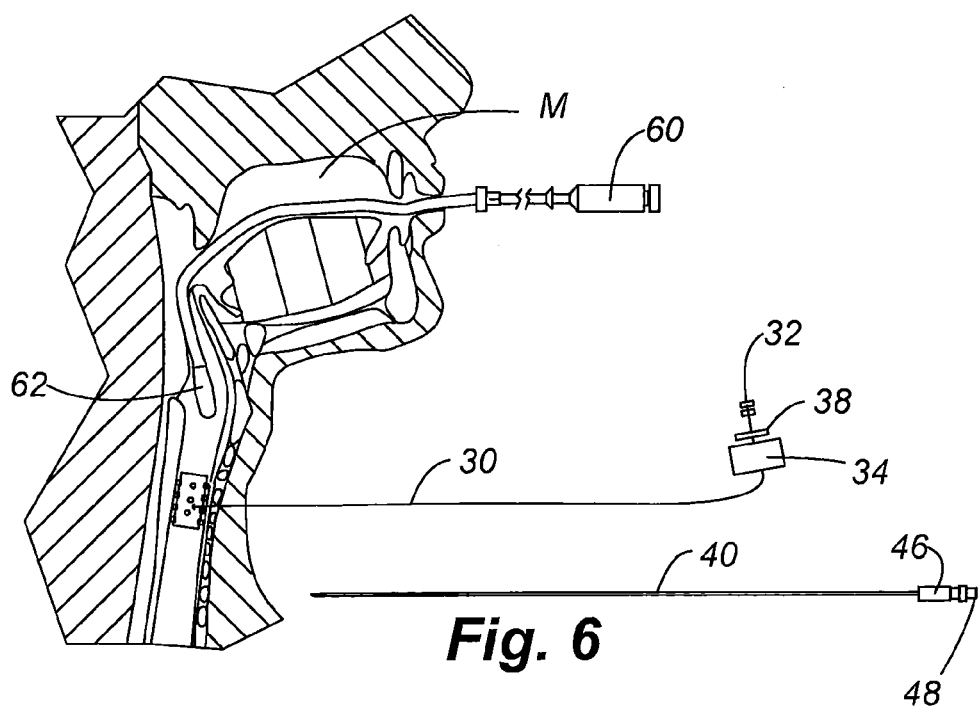
FIG. 6 is another vertical section illustrating the needle removed from the patient and the suture extending through the patient's neck.
Figure 7:
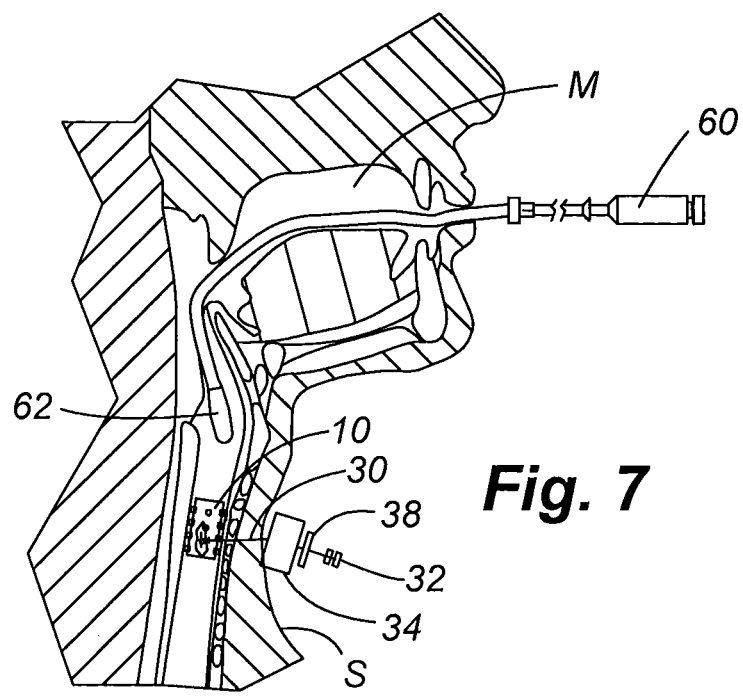
FIG. 7 is another vertical section illustrating the pledget and suture clamps moved along the suture and placed adjacent the patient's neck.
Figure 8:
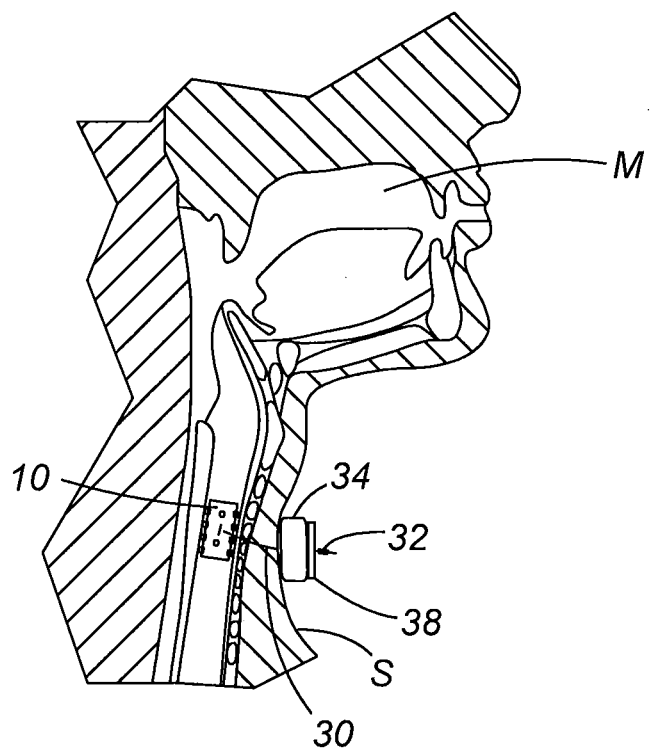
FIG. 8 is another vertical section illustrating the pledget placed against the patient's neck with the clamps securing the exposed end of the suture to the pledget.
Figure 9:
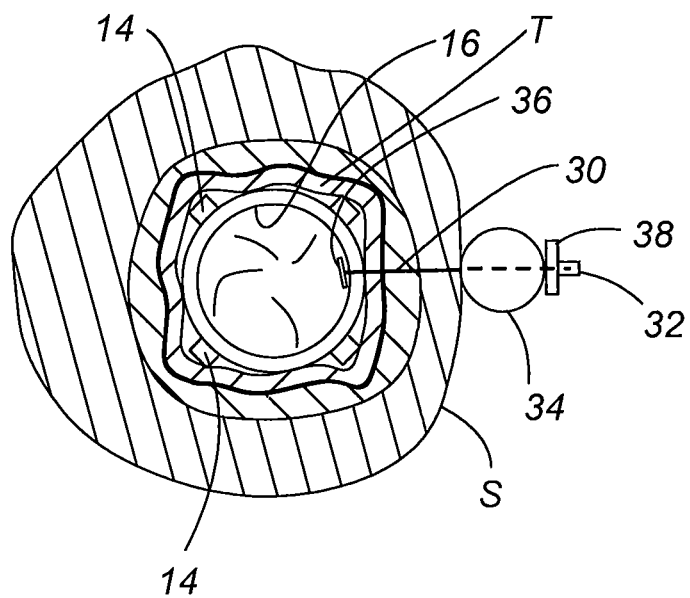
FIG. 9 is another horizontal section illustrating the suture tightened with the pledget placed against the neck and the clamps holding the tightened suture against the pledget.

Referring to FIG. 6, the introducer needle is then withdrawn thereby leaving the suture 30 anchored within the stent. Referring to FIG. 7, the pledget 34, washer 38 and clamp(s) 32 can then be slid along the suture and positioned adjacent the exterior surface of the neck. Referring to FIGS. 8 and 9, the suture is tightened and the pledget, washer, and clamp 32 are further slid along the suture and the pledget contacts the neck. The suture is tensioned a desired amount to account for normal movement of the patient's neck. If the suture is overtightened, the patient may experience discomfort so it is preferable to not over-tighten the suture. The clamp(s) 32 is activated to hold the suture against the washer and pledget, and any remaining length of the suture 30 may be clipped. As best seen in FIG. 9, when the suture is tensioned, the T-bar 36 is secured against the interior surface 16 of the stent, thereby providing a simple, but effective anchor to hold the stent within a desired position in the trachea. FIG. 9 also shows the pledget 34 placed against the surface of the neck with the washer 38 placed between the pledget and the clamp(s) 32.

Although a single suture anchor is illustrated, it is also contemplated that more than one suture anchor could be used to secure the stent within the trachea. Particularly for longer tracheal stents, it may be advantageous to use more than a single suture anchor. Furthermore, it is contemplated that the suture anchor can be oriented through the neck of the patient at a desired angle in order to avoid interference with other physical features of the patient. The Figures show the suture extending substantially perpendicular to the length of the stent, but the suture can be oriented at angles.

With respect to the method of the present invention, a patient P can be placed under general anesthesia in an operative suite. The tracheal stenosis may be first treated with rigid bronchoscopic expansion and/or balloon dilation prior to placement of the stent. The airway is measured, and then fitted with an appropriately sized stent having a selected diameter. The stent may be deployed utilizing a stent deployment plunger (not shown) to place the stent. Adjustment of the stent in the trachea can be accomplished by rigid forceps (not shown). Once the stent is located in the optimal position with good tracheal wall apposition, the bronchoscope can be removed, and a laryngeal mask (not shown) can be inserted into the larynx to manage the airway of the patient during the procedure. A laryngeal mask typically includes a tube with an inflatable cuff that is inserted into the pharynx. A flexible bronchoscope is inserted into the trachea and an imaging camera located at the distal end of the bronchoscope is positioned to view the stent.

The T-bar of the suture is loaded in the open distal end of the introducer needle. The skin surface of the patient is sterilized. Under flexible bronchoscopic visualization, the needle is then inserted through the neck and through wall of the stent. The T-bar is deployed, for example by use of the stylet, thereby separating the T-bar from the introducer needle. The introducer needle is then removed from the neck of the patient. The suture is tightened until the T-bar is placed flush against the interior wall of the stent. The pledget and washer are slid along the suture so the pledget is placed against the neck. The suture is tightened again and then clamped to attach the free end of the suture against the washer and pledget. A small amount of play can be left in the suture to allow for movement of suture within the neck and to accommodate the swallowing motion of the patient.

A variety of materials are contemplated for the stent and integral anchor. For the tracheal stent, it is known to use silicone as a preferred material. The T-bar 36 may be made of a suitable plastic or stainless steel material. The T-bar can also be a silicone bead that is attached as by thermal bonding to the end of the suture material. The suture 30 can be made of conventional suture material. Alternatively, in order to avoid potential complications of cellulitis and suture breakage, the suture can be made of a synthetic material.

In accordance with the apparatus and method of the invention, placement of a tracheal stent with a suture anchor can be an effective modality for the treatment of benign tracheal stenosis. Even with stents that may have outer surface studs, there can still be some migration of the stent and the suture anchor prevents such migration.

Placement of the suture anchor is done easily under bronchoscopic visualization adding very little time and expense to the overall procedure. The suture is relatively non-intrusive, requiring only a very small opening to be made in the neck of the patient.

Although the apparatus and method of the present invention have been disclosed with respect to preferred embodiments, it shall be understood that various other changes and modifications may be made within the spirit and scope of the present invention, taking into consideration the scope of the appended claims.

What is claimed is:

1. In combination, an airway stent and an integral anchor, comprising:
    a stent body having a cylindrical shape, and proximal and distal ends;
    a suture anchor secured to said stent body, said suture anchor comprising a length of suture, a T-bar element secured to a distal end of the length of suture and said T-bar element placed within a hollow interior space of the stent body, and said length of suture extending through a wall of the stent body;
    a pad having an opening to receive the suture;
    a plurality of studs disposed on an exterior surface of said stent body and selectively spaced along said stent body for improving frictional engagement of the stent within the airway;
    at least one of a clamp or knot securing an end of the suture against the pad;
    wherein said suture is of a sufficient length to further extend substantially horizontally through a neck of a patient, and said pad being positioned externally against the neck of the patient.

2. The combination, as claimed in claim 1, further including:
    a washer placed over the length of suture and between the clamp and the pad.

3. The combination, as claimed in claim 1, wherein:
    the proximal and distal ends of the stent body extend substantially transversely to a length of the body.

4. In combination, an airway stent and an integral anchor, comprising:
    a stent body having a cylindrical shape, and proximal and distal ends;
    a suture anchor secured to said stent body, said suture anchor comprising a length of suture, an anchor element secured to a distal end of the length of suture and said anchor element placed within a hollow interior space of the stent body, and said length of suture extending through a wall of the stent body;
    a pad having an opening to receive the suture;
    a plurality of studs disposed on an exterior surface of said stent body and selectively spaced along said stent body for improving frictional engagement of the stent within the airway;
    means for securing an end of the suture against the pad;
    a washer placed over the length of suture and between the means for securing and end of the suture and the pad; and
    wherein said suture is of a sufficient length to further extend substantially horizontally through a neck of a patient, and said pad being positioned externally against the neck of the patient.

5. The combination, as claimed in claim 4, wherein:
    said anchor includes a T-bar element.

* * * * *